United States Patent
Neumann

(10) Patent No.: US 11,594,316 B2
(45) Date of Patent: Feb. 28, 2023

(54) METHODS AND SYSTEMS FOR NUTRITIONAL RECOMMENDATION USING ARTIFICIAL INTELLIGENCE ANALYSIS OF IMMUNE IMPACTS

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 19 days.

(21) Appl. No.: 16/865,740

(22) Filed: May 4, 2020

(65) Prior Publication Data

US 2021/0343392 A1 Nov. 4, 2021

(51) Int. Cl.
*G16H 20/60* (2018.01)
*G06N 20/00* (2019.01)

(52) U.S. Cl.
CPC .............. *G16H 20/60* (2018.01); *G06N 20/00* (2019.01)

(58) Field of Classification Search
CPC .... G06N 5/04; G06Q 50/22–24; G16H 50/20; A63B 43/004; G06F 16/906
See application file for complete search history.

(56) References Cited

U.S. PATENT DOCUMENTS

| | | | |
|---|---|---|---|
| 7,894,849 B2 | 2/2011 | Kass et al. | |
| 8,409,104 B2 | 4/2013 | Cobain | |
| 8,532,938 B2 | 9/2013 | Jung et al. | |
| 8,737,971 B2 | 5/2014 | Van Rooyen | |
| 8,762,167 B2 | 6/2014 | Blander et al. | |
| 8,822,225 B2 | 9/2014 | Gotch et al. | |
| 9,132,219 B2 | 9/2015 | Akonur et al. | |
| 9,183,757 B2 | 11/2015 | Yamada et al. | |
| 9,589,480 B2 | 3/2017 | Ellis | |
| 9,730,660 B2 * | 8/2017 | Suzuki | ................ A61B 6/5211 |
| 9,758,839 B2 | 9/2017 | Apte et al. | |

(Continued)

FOREIGN PATENT DOCUMENTS

WO 2018020239 2/2018

OTHER PUBLICATIONS

Westerman, et al.; Longitudinal analysis of biomarker data from a personalized nutrition platform in healthy subjects; Scientific Reports; Oct. 2, 2018; https://www.nature.com/articles/s41598-018-33008-7.pdf.

(Continued)

*Primary Examiner* — Robert W Morgan
*Assistant Examiner* — Edward B Winston, III
(74) *Attorney, Agent, or Firm* — Caldwell Intellectual Property Law

(57) ABSTRACT

A system for nutritional recommendation using artificial intelligence analysis of immune impacts includes a computing device designed and configured to receive a test result detecting an effect of at least an aliment on at least a biomarker, determine an immune system impact of the at least an aliment as a function of the at least a biomarker using a machine-learning process, the machine-learning process trained using a first training set relating biomarker levels to immune system function, generate a nutritional recommendation using the determined immune system impact, and provide the nutritional recommendation to the user.

16 Claims, 5 Drawing Sheets

(56) References Cited

U.S. PATENT DOCUMENTS

| | | | |
|---|---|---|---|
| 9,838,508 B2 | 12/2017 | Salem | |
| 10,102,345 B2 | 10/2018 | Yanev et al. | |
| 10,127,361 B2 | 11/2018 | Hyde et al. | |
| 10,133,849 B2 | 11/2018 | Yanev et al. | |
| 10,361,003 B2* | 7/2019 | Segal | G06N 20/20 |
| 10,553,319 B1* | 2/2020 | Neumann | G16H 50/20 |
| 10,559,386 B1* | 2/2020 | Neumann | G06F 16/906 |
| 10,568,570 B1* | 2/2020 | Sherpa | G16H 50/50 |
| 11,185,283 B2* | 11/2021 | Hadley | A61B 5/749 |
| 2008/0177149 A1 | 7/2008 | Weinert et al. | |
| 2008/0195594 A1 | 8/2008 | Gerjets et al. | |
| 2008/0306763 A1 | 12/2008 | James | |
| 2010/0098809 A1 | 4/2010 | Bender et al. | |
| 2012/0130732 A1* | 5/2012 | Blander | G16H 20/30 705/2 |
| 2012/0136680 A1* | 5/2012 | Lombard | G16H 20/10 705/3 |
| 2013/0079612 A1 | 3/2013 | Hunt et al. | |
| 2013/0138447 A1 | 5/2013 | Nova et al. | |
| 2015/0012295 A1 | 1/2015 | Mahoney | |
| 2016/0042152 A1 | 2/2016 | Oran | |
| 2017/0216518 A1 | 8/2017 | Davis et al. | |
| 2018/0001184 A1* | 1/2018 | Tran | G09B 19/0038 |
| 2018/0032698 A1 | 2/2018 | Lau et al. | |
| 2019/0340754 A1* | 11/2019 | Honkala | G06V 10/82 |
| 2019/0371474 A1* | 12/2019 | Borsic | G16H 50/50 |
| 2020/0065681 A1* | 2/2020 | Wolf | G06N 5/04 |
| 2020/0261009 A1* | 8/2020 | Everman | G01L 9/00 |
| 2020/0398083 A1* | 12/2020 | Adelsheim | A61N 5/1075 |

OTHER PUBLICATIONS

Inside Tracker; Who we are; file:///C:/Users/LindseyPowell/Downloads/InsideTracker's%20expert%20team_%20scientists . . . pdf.

Bald, Eric; The A.I. Diet; https://www.weizmann-usa.org/news-media/in-the-news/the-ai-diet.

Ramachandran, Swaroopini; Mar. 15, 2019; The algorithm to a perfect diet—AI has answers; http://peasonmoss.com/2019/03/15/the-algorithm-to-a-perfect-diet-ai-has-answers/.

Vk, Anirudh; 5 AI-Powered fitness startups in India who are using data science to promote healthy lifestyle; https://www.analyticsindiamag.com/5-ai-powered-fitness-startups-in-india-who-are-using-data-science-to-promote-healthy-lifestyle/.

* cited by examiner

METHODS AND SYSTEMS FOR NUTRITIONAL RECOMMENDATION USING ARTIFICIAL INTELLIGENCE ANALYSIS OF IMMUNE IMPACTS

FIELD OF THE INVENTION

The present invention generally relates to the field of artificial intelligence. In particular, the present invention is directed to methods and systems for nutritional recommendation using artificial intelligence analysis of immune impacts.

BACKGROUND

Design of systems for analysis of immune data is often frustrated by the extreme complexity and variability of the subject matter. A vast multiplicity of factors to be measured is further complicated by a complex web of subtle but crucial interactions. Worse still a given factor may vary widely in significance between subjects, in ways that can frustrate consistent application of analytical techniques

SUMMARY OF THE DISCLOSURE

In an aspect, a system for nutritional recommendation using artificial intelligence analysis of immune impacts includes a computing device designed and configured to receive a test result detecting an effect of at least an aliment on at least a biomarker, determine an immune system impact of the at least an aliment as a function of the at least a biomarker using a machine-learning process, the machine-learning process trained using a first training set relating biomarker levels to immune system function, generate a nutritional recommendation using the determined immune system impact, and provide the nutritional recommendation to the user.

In another aspect, a method of nutritional recommendation using artificial intelligence analysis of immune impacts includes receiving, by a computing device, a test result detecting an effect of at least an aliment on at least a biomarker. The method includes determining, by the computing device, an immune system impact of the at least an aliment as a function of the at least a biomarker using a machine-learning process, the machine-learning process trained using a first training set relating biomarker levels to immune system function. The method includes generating, by the computing device, a nutritional recommendation using the determined immune system impact. The method includes providing, by the computing device, the nutritional recommendation to the user.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Embodiments use testing inputs, which may be differential testing inputs to associated aliments and/or clusters of aliments with levels and/or changes in biomarkers. A machine-learning algorithm determines an immune impact associated with such changes. Training data associated with machine-learning algorithms, classification algorithms, and/or clustering algorithms may be limited to matching subsets.

Figure 1:
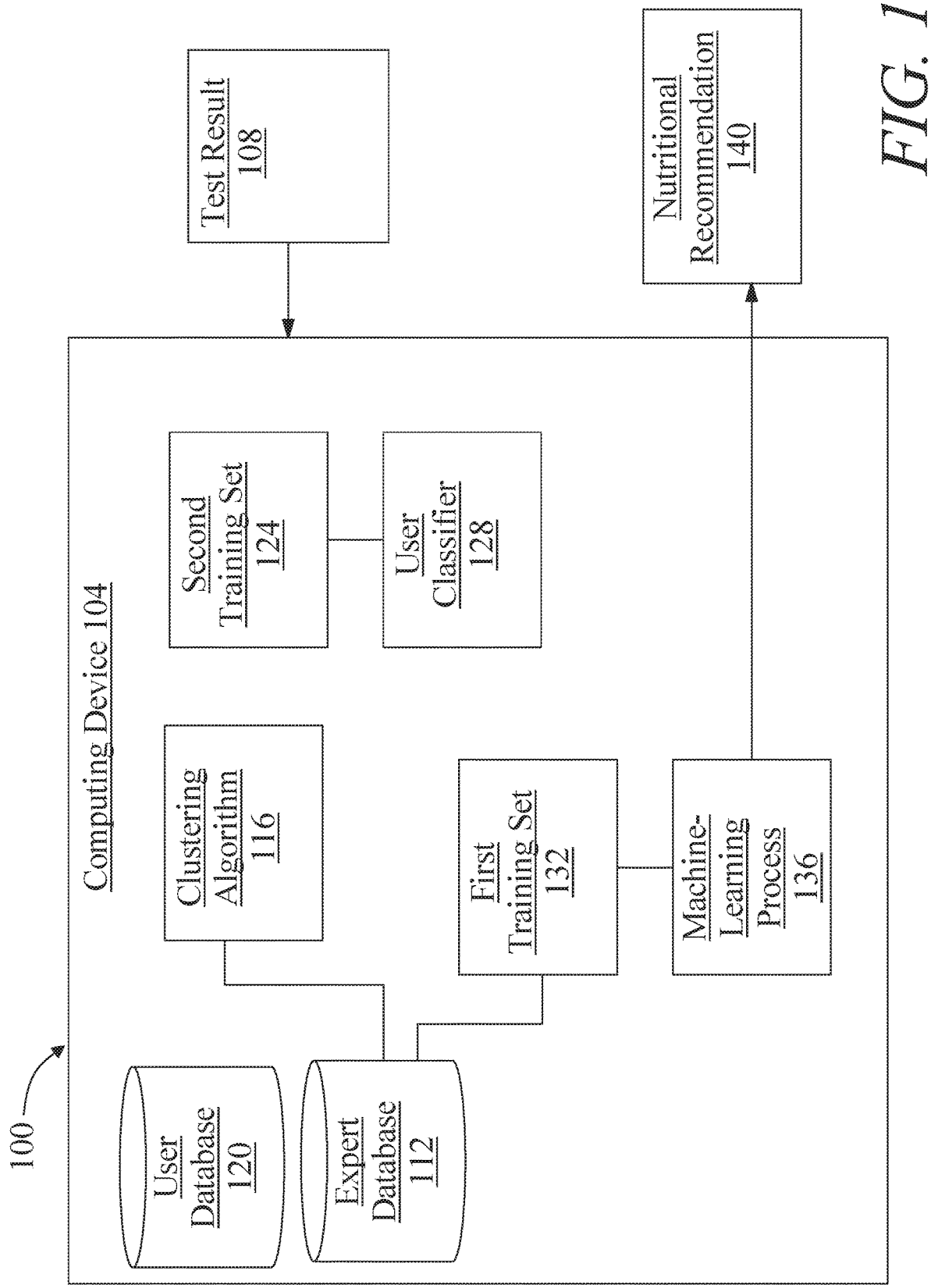
FIG. 1 is a block diagram of an exemplary embodiment of a system for nutritional recommendation using artificial intelligence analysis of immune impacts.

Referring now to FIG. 1, an exemplary embodiment of a system 100 for nutritional recommendation using artificial intelligence analysis of immune impacts is illustrated. System includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently, or may include two or more computing device 104 operating in concert, in parallel, sequentially or the like; two or more computing device 104 may be included together in a single computing device 104 or in two or more computing device 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing device, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing device in a first location and a second computing device 104 or cluster of computing device in a second location. Computing device 104 may include one or more computing device dedicated to data storage, security, distribution of traffic for load balancing, and the like. Computing device 104 may distribute one or more computing tasks as described below across a plurality of computing device of computing device 104, which may operate in parallel, in series, redundantly, or in any other manner used for distribution of tasks or memory between computing device. Computing device 104 may be implemented using a "shared nothing" architecture in which data is cached at the worker, in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 may be designed and configured to receive a test result 108 detecting an effect of a physiological stimulus on at least a biomarker. A "physiological stimulus," as used in this disclosure, is an action that affects a user's physiological status, including without limitation intake of food, drink, water, nutrients in consumable form, supplements, a modification to a sleep routine of the user, fitness activity such as exercise, other wellness-related activity such as meditation, psychological influences that have physiological effect such as therapy or lifestyle changes, and/or pharmaceutical products.

As a non-limiting example, and further referring to FIG. 1, detecting effect of a physiological stimulus may include detecting an effect of at least an aliment on at least a biomarker. An "aliment," as used in this disclosure, is a comestible material. An aliment may include without limitation any food, drink, or other product that may be eaten or drunk. An aliment may include an individual ingredient, a combination of multiple ingredients, and/or one or more ingredients to which a given process of preparation, such as cooking, marinating, or otherwise altering the ingredients, has been performed. In an embodiment, processes described in this disclosure may provide information regarding immune effects of individual ingredients, combinations of ingredients, particular dishes and/or products created using combinations of ingredients and/or processes performed on one or more ingredients, combinations of such dishes and/or products into meals, meal plans, or other spatially or temporally coincident consumption processes and/or combinations, or the like, each of which may be considered an aliment for the purposes of this disclosure.

Still referring to FIG. 1, a "biomarker," as used in this disclosure, is a measurable substance and/or element of physiological data in an a human subject whose presence is indicative of some phenomenon such as disease, infection, state of health of one or more systems within a human body, and/or degree of efficacy of immune system. At least a biomarker may include, without limitation, hemoglobin A1c (HbA1c), red blood cell magnesium, serum magnesium, complete blood count, red blood cell count, white blood cell count, vitamin D, ferritin, cortisol, high sensitivity C reactive protein (hsCRP), alanine aminotransferase (ALT), glucose, hemoglobin A1c, DHEAS, and/or testosterone. At least a biomarker may alternatively or additionally include measures of microbiome, physiological markers such as heart rate variability, pulse, pressure, body mass index, and/or any other element of physiological data and/or biological extraction, for instance as described in U.S. Nonprovisional application Ser. No. 16/659,817, filed on Oct. 22, 2019, and entitled "METHODS AND SYSTEMS FOR IDENTIFYING COMPATIBLE MEAL OPTIONS," the entirety of which is incorporated herein by reference.

With continued reference to FIG. 1, system and/or computing device 104 may select at least a biomarker with regard to which test may be performed; without limitation, selected at least a biomarker may be transmitted to user and/or a person, entity, and/or device performing testing. Alternatively or additionally, existing testing results saved, for instance, in a database and/or otherwise available to computing device 104 may be retrieved according to selection of at least a biomarker. Selection of at least a biomarker may be performed according to a score or other quantitative datum indicating a degree of impact and/or effect on immune system efficacy and/or association therewith; in other words, quantitative datum and/or score may indicate a degree to which a given measurement and/or level of a given biomarker may be correlative with a degree of efficacy and/or health of a person's immune system. At least a biomarker may be selected where quantitative datum and/or score exceeds a preconfigured threshold. Any of preconfigured threshold, quantitative datum, and/or score may be provided by one or more expert inputs, which may be received directly from expert submissions via user interface forms or the like, and/or retrieved from an expert database 112 recording such expert submissions.

Figure 2:
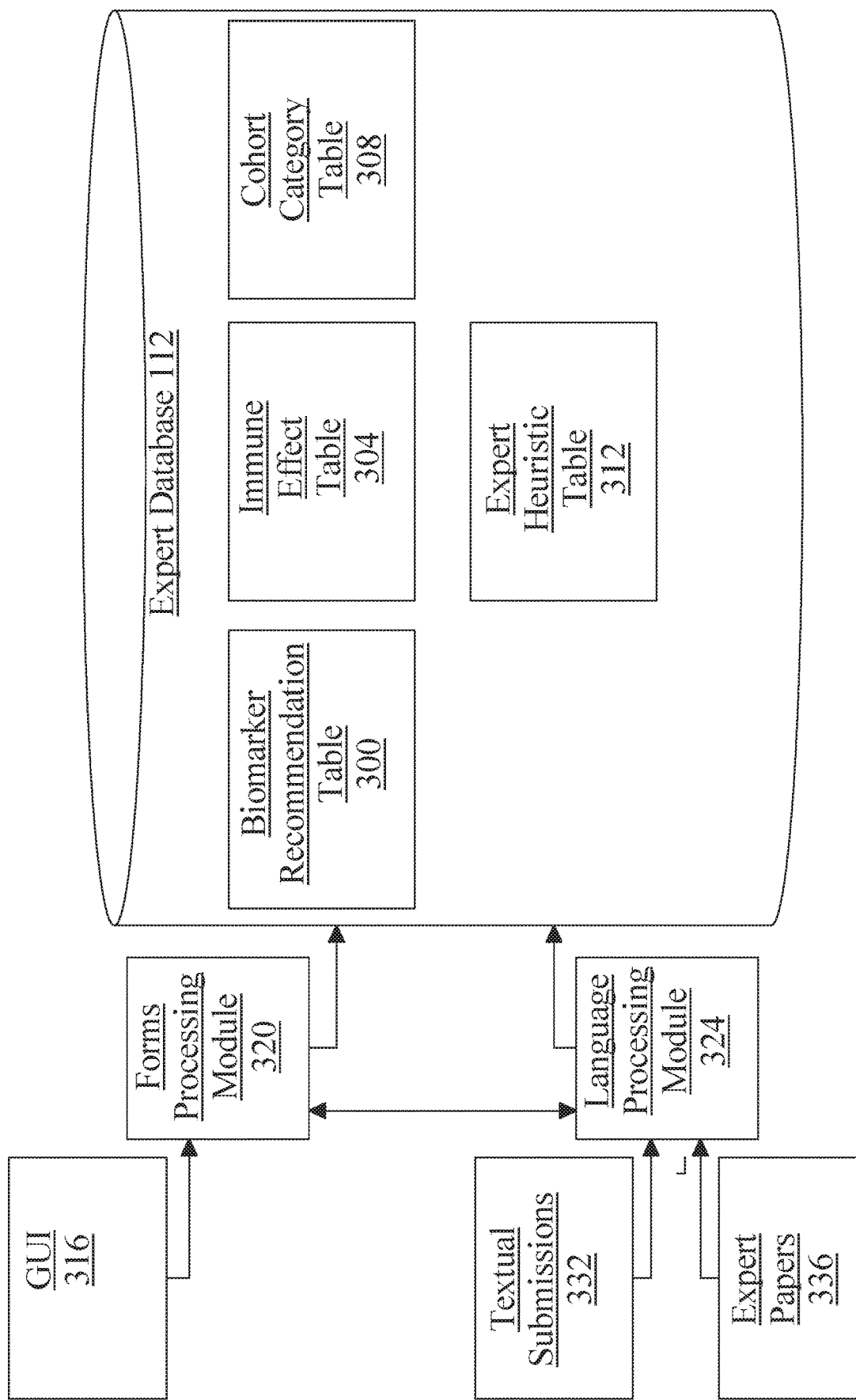
FIG. 2 is a block diagram of an exemplary embodiment of an expert database.

Referring now to FIG. 2, an exemplary embodiment of an expert database 112 is illustrated. Expert database 112 may, as a non-limiting example, organize data stored in the expert database 112 according to one or more database tables. One or more database tables may be linked to one another by, for instance, common column values. For instance, a common column between two tables of expert database 112 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 2, one or more database tables in expert database 112 may include, as a non-limiting example, a biomarker recommendation table 200, which may include biomarkers recommended for use in predicting immune system impact and/or efficacy, expert entries indicating degrees of relevance to and/or efficacy in predicting immune impacts, and/or other elements of data computing device 104 and/or system 100 may use to determine usefulness and/or relevance of biomarkers in tests as described in this disclosure. One or more tables may include an immune effect table 204, which may link biomarker levels and/or combinations thereof to one or more measures of immune impact; immune effect table 204 may contain a plurality of expert entries associating biomarker levels with immune system function. One or more tables may include, without limitation, a cohort category table 208 which may contain one or more expert input identifying one or more categories of data, such as demographic data, medical history data, physiological data such as biological extraction data, or the like, with regard to which users having matching or similar data may be expected to have similar immune responses and/or immune effects as a result of consuming food elements and/or other aliments. One or more tables may include, without limitation, an expert heuristic table 212, which may include one or more expert inputs describing potential mathematical relationships between biomarkers and immune effects, between rapidly changing biomarkers and chronic biomarkers as described in further detail below, or the like.

In an embodiment, and still referring to FIG. 2, a graphical user interface 216 may receive expert submissions for inclusion in expert database 112. A forms processing module 220 may sort data entered in a submission via a graphical user interface receiving expert submissions by, for instance, sorting data from entries in the graphical user interface to related categories of data for insertion into one or more tables of expert database 112 and/or use as expert submissions as set forth in this disclosure. Where data is chosen by an expert from pre-selected entries such as drop-down lists, data may be stored directly; where data is entered in textual form, a language processing module 224 may be used to map data to an appropriate existing label, for instance using a vector similarity test or other synonym-sensitive language processing test to map data to existing labels and/or categories. Similarly, data from an expert textual submissions 232, such as accomplished by filling out a paper or PDF form and/or submitting narrative information, may likewise be processed using language processing module 224.

Still referring to FIG. 2, a language processing module 224 may include any hardware and/or software module. Language processing module 224 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 2, language processing module 224 may compare extracted words to categories of data to be analyzed; such data for comparison may be entered on computing device 104 as described above using expert data inputs or the like. In an embodiment, one or more categories may be enumerated, to find total count of mentions in such documents. Alternatively or additionally, language processing module 224 may operate to produce a language processing model. Language processing model may include a program automatically generated by at least a server and/or language processing module 224 to produce associations between one or more words extracted from at least a document and detect associations, including without limitation mathematical associations, between such words, and/or associations between such words and other elements of data analyzed, processed and/or stored by system 100. Associations between language elements, may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of data; positive or negative indication may include an indication that a given document is or is not indicating a category of data.

Still referring to FIG. 2, language processing module 224 and/or computing device 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 224 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 2, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 2, language processing module 224 may use a corpus of documents to generate associations between language elements in a language processing module 224, and computing device 104 may then use such associations to analyze words extracted from one or more documents. Documents may be entered into classification device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, classification device may automatically obtain the document using such an identifier, for instance by submitting a request to a database or compendium of documents such as JSTOR as provided by Ithaka Harbors, Inc. of New York.

Data may be extracted from expert papers 236, which may include without limitation publications in medical and/or scientific journals, by language processing module 224 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

Referring again to FIG. 1, computing device 104 may be configured to receive the test result 108 by receiving a result of a differential test. A "differential test," as used in this disclosure, is a test performed by finding a first level of at least a biomarker prior to user receipt of a physiological stimulus, such as without limitation consumption of at least an aliment, finding a second level of the at least a biomarker after user receipt of the physiological stimulus, such as without limitation consumption of the at least an aliment, and recording a difference between the first test and the second test. A differential test may be performed by comparing a baseline value from previous tests to a currently measured value, by comparing a value taken in a first sample of at least a biomarker taken prior to user receipt of physiological stimulus such as consumption of at least an aliment to a value taken in a second sample of the at least a biomarker taken after user receipt of physiological stimulus such as consumption of the at least an aliment, or the like. Differential test may be performed with regard to multiple samples taken in a series of tests over time.

Continuing to refer to FIG. 1, at least a biomarker may include a plurality of biomarkers, such as a panel of biomarkers containing biomarkers recommended via expert entries as described above; panel and/or plurality may include all biomarkers having an expert-submitted immune impact greater than a threshold as described above. Alternatively or additionally, experts may recommend one or more panels of biomarkers, and computing device 104 and/or system 100 may determine that the one or more panels of biomarkers are the at least a biomarker by comparison and/or receipt of expert entries. Computing device 104 and/or system 100 may perform one or more processes of statistical analysis and/or machine learning with regard to expert entries; for instance, computing device 104 and/or system may compare biomarker impacts and/or biomarker panel impacts generated by averaging or otherwise statistically aggregating expert-input impacts to thresholds. Alternatively or additionally each biomarker and/or panel may have a score and/or quantitative datum indicative of its degree of impact, which computing device 104 and/or system 100 may calculate using a supervised machine-learning process as described below; supervised machine-learning process may be trained using training data containing expert inputs as described above.

In an embodiment, and still referring to FIG. 1, computing device 104 may be further configured to receive the test result 108 by identifying at least cluster of physiological stimuli, such as for example a cluster of foods, exercises, supplements, medications, or the like having similar biomarker effects to the at least a physiological stimulus and/or at least an aliment using a clustering algorithm 116 and a second training set 124 representing biomarker impacts of physiological stimuli and/or foods, for instance as received in expert inputs as described above on a population of human subjects, and selecting as the at least a physiological stimulus and/or at least an aliment at least a cluster representative. A cluster of foods and/or other physiological stimuli may be identified using a clustering algorithm 116, defined for the purposes of this disclosure as an algorithm that groups elements of data according to a measure of distance and/or similarity; in an embodiment, computing device 104 may perform a clustering algorithm 116 that groups foods and/or other physiological stimuli according to an effect of those foods and/or other physiological stimuli on one or more biomarkers.

Continuing refer to FIG. 1, and as a non-limiting, illustrative example, a clustering algorithm 116 may be implemented using a k-means clustering algorithm 116. A "k-means clustering algorithm" as used in this disclosure, includes cluster analysis that partitions n observations or unclassified cluster data entries into k clusters in which each observation or unclassified cluster data entry belongs to the cluster with the nearest mean, using, for instance behavioral training set as described above. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster; for instance, and without limitation, a fuzzy clustering algorithm 116 may be used to identify clustering of gene combinations with multiple disease states, and vice versa. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, computing device 104 may generate a k-means clustering algorithm 116 receiving unclassified user data, such as without limitation biological extraction data, and outputs a definite number of classified data entry clusters wherein the data entry clusters each contain cluster data entries. K-means algorithm may select a specific number of groups or clusters to output, identified by a variable "k." Generating a k-means clustering algorithm 116 includes assigning inputs containing unclassified data to a "k-group" or "k-cluster" based on feature similarity. Centroids of k-groups or k-clusters may be utilized to generate classified data entry cluster. K-means clustering algorithm 116 may select and/or be provided "k" variable by calculating k-means clustering algorithm 116 for a range of k values and comparing results. K-means clustering algorithm 116 may compare results across different values of k as the mean distance between cluster data entries and cluster centroid. K-means clustering algorithm 116 may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering algorithm 116 may act to identify clusters of foods and/or other physiological stimuli having similar effects on a biomarker; in an embodiment, the effect may vary from one user to another, but a difference in effect for a given user from one food and/or other physiological stimulus to another food and/or physiological stimulus in the cluster may be minimal and/or small enough to cause inclusion in a cluster. In other words, two foods and/or physiological stimuli in a cluster may be expected to have similar effects to each other on a biomarker and/or set of biomarkers when received and/or consumed by a given user.

With continued reference to FIG. 1, generating a k-means clustering algorithm 116 may include generating initial estimates for k centroids which may be randomly generated or randomly selected from unclassified data input. K centroids may be utilized to define one or more clusters. K-means clustering algorithm 116 may assign unclassified data to one or more k-centroids based on the squared Euclidean distance by first performing a data assigned step of unclassified data. K-means clustering algorithm 116 may assign unclassified data to its nearest centroid based on the collection of centroids $c_i$ of centroids in set C. Unclassified data may be assigned to a cluster based on $\text{argmin}_{c_i \ni C} \text{dist}(c_i, x)^2$, where argmin includes argument of the minimum, $c_i$ includes a collection of centroids in a set C, and dist includes standard Euclidean distance. K-means clustering module may then recompute centroids by taking mean of all cluster data entries assigned to a centroid's cluster. This may be calculated based on $c_i = 1/|S_i| \Sigma x_i \ni S_i^{x_i}$. K-means clustering algorithm 116 may continue to repeat these calculations until a stopping criterion has been satisfied such as when cluster data entries do not change clusters, the sum of the distances have been minimized, and/or some maximum number of iterations has been reached.

Still referring to FIG. 1, k-means clustering algorithm 116 may be configured to calculate a degree of similarity index value. A "degree of similarity index value" as used in this disclosure, includes a distance measurement indicating a measurement between each data entry cluster generated by k-means clustering algorithm 116 and a selected data set. Degree of similarity index value may indicate how close an element or set of elements of user data is to being classified by k-means algorithm to a particular cluster. K-means clustering algorithm 116 may evaluate the distances of user data to the k-number of clusters output by k-means clustering algorithm 116. Short distances between a set of data regarding a food and a cluster may indicate a higher degree of similarity between the food data and a particular cluster. Longer distances between a set of data regarding a food and a cluster may indicate a lower degree of similarity between the food data and a particular cluster.

With continued reference to FIG. 1, k-means clustering algorithm 116 may select a classified data entry cluster as a function of the degree of similarity index value. In an embodiment, k-means clustering algorithm 116 may select a classified data entry cluster with the smallest degree of similarity index value indicating a high degree of similarity between user data and the data cluster. Alternatively or additionally k-means clustering algorithm 116 may select a plurality of clusters having low degree of similarity index values to user data sets, indicative of greater degrees of similarity. Degree of similarity index values may be compared to a threshold number indicating a minimal degree of relatedness suitable for inclusion of a set of food data and/or physiological stimulus data in a cluster, where degree of similarity indices falling under the threshold number may be included as indicative of high degrees of relatedness. The above-described illustration of clustering using k-means clustering is included for illustrative purposes only, and should not be construed as limiting potential implementation of clustering; persons skilled in the art, upon reviewing the entirety of this disclosure, will be aware of various additional or alternative clustering approaches that may be used consistently with this disclosure.

Still referring to FIG. 1, computing device 104 may select each physiological stimulus of the at least a physiological stimulus and/or each aliment of the at least an aliment as a representative of a cluster. For instance, and without limitation, clustering algorithm 116 may identify a plurality of clusters of foods and/or physiological stimuli that, for a population of human subjects, represent a plurality of categories of impact on immune system. A food and/or stimulus from each cluster may be selected; food and/or physiological stimulus may be selected for instance as a food and/or physiological stimulus closest to a centroid, a food and/or physiological stimulus having a degree of impact or other numerical measure closest to an arithmetic and/or multiplicative mean of foods and/or physiological stimuli in cluster, or the like. Alternatively or additionally, computing device 104 may present to a user a list of foods and/or physiological stimuli from each cluster; user may select a cluster representative from each cluster to use in testing as at least an aliment and/or at least a physiological stimulus. This may aid in ensuring user compliance, as well as permitting user to select foods and/or physiological stimuli that are available and/or affordable for user to use in testing.

In an embodiment, and continuing to refer to FIG. 1, selecting the physiological stimulus and/or at least an aliment may include selecting a first candidate cluster representative, determining a user-specific proscription of the first candidate cluster representative, and selecting a substitute item as the cluster representative. A "user-specific proscription," as used in this disclosure, is an element of data indicating that a user cannot receive a physiological stimulus; for instance, where the physiological stimulus is an aliment, a user-specific proscription is an element of data indicating that a user cannot consume a given food or other aliment. A user-specific proscription may include, without limitation, a health-related reason the user receive the physiological stimulus and/or cannot consume the food or other aliment, such as an allergy, sensitivity, or other medical condition such as without limitation phenylketonuria, a medical condition preventing participation in an activity and/or receipt of a pharmaceutical product, a moral, religious, and/or philosophical prohibition on receipt of physiological stimulus and/or consumption of a food or other aliment, or the like.

Still referring to FIG. 1, user information, including without limitation past test results 108, biomarker levels, eating habits exercise habits, lifestyle habits, medical history, demographic information, and/or user-specific proscriptions may be stored in a user database 120. User database 120 may include any data structure for ordered storage and retrieval of data, which may be implemented as a hardware or software module. A user database 120 may be implemented, without limitation, as a relational database, a key-value retrieval datastore such as a NOSQL database, or any other format or structure for use as a datastore that a person skilled in the art would recognize as suitable upon review of the entirety of this disclosure. A user database 120 may include a plurality of data entries and/or records corresponding to user tests as described above. Data entries in a user database 120 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a user database 120 may reflect categories, cohorts, and/or populations of data consistently with this disclosure. User database 120 may be located in memory of computing device 104 and/or on another device in and/or in communication with system 100.

Figure 3:
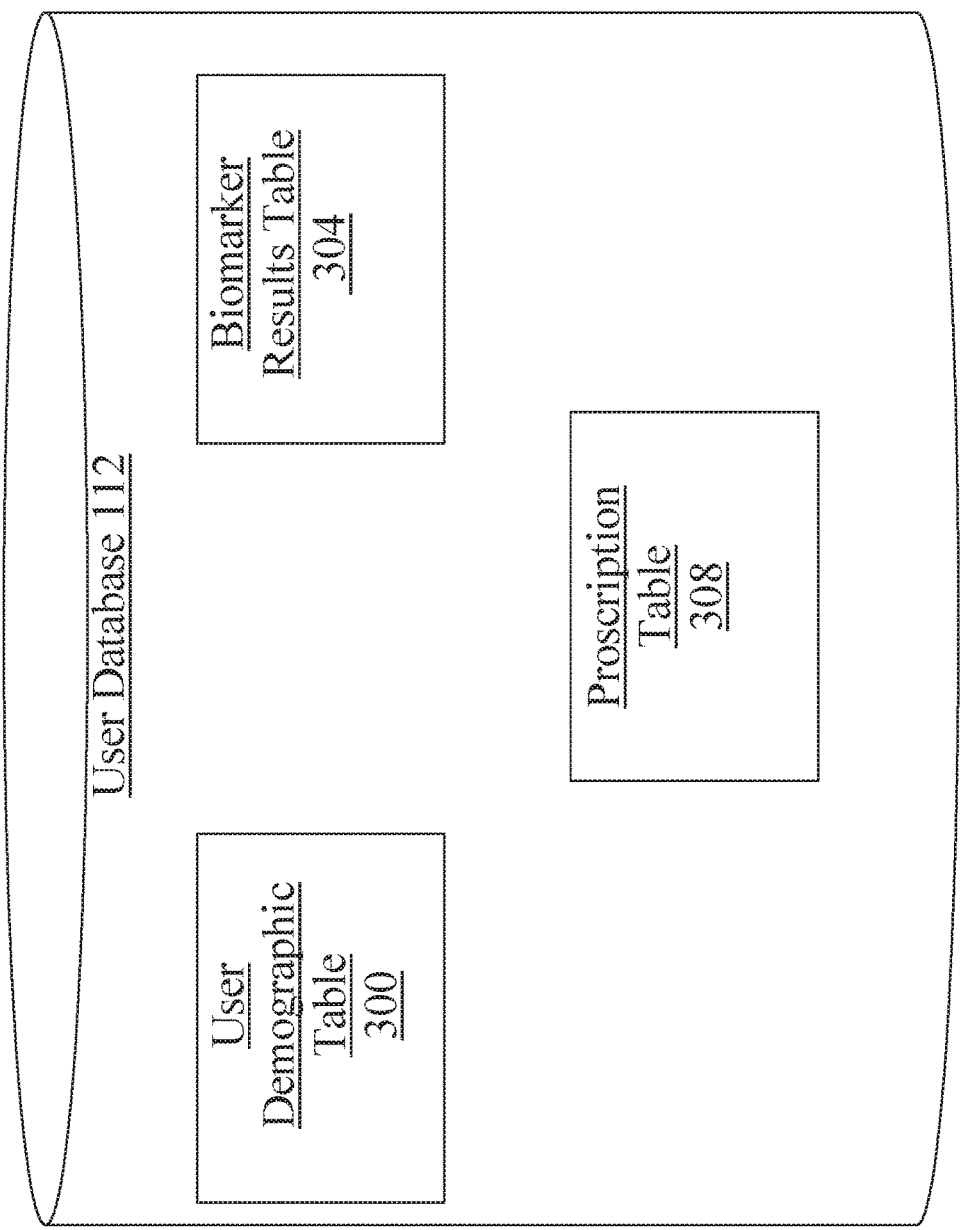
FIG. 3 is a block diagram of an exemplary embodiment of a user database.

Referring now to FIG. 3, an exemplary embodiment of a user database 120 is illustrated. One or more tables in user database 120 may include, without limitation, a user demographic table 300, which may be used to store one or more elements of demographic information concerning users, such as age, ethnicity, sex, nation of residence, national origin, or the like. One or more tables in user database 120 may include, without limitation, biomarker results table 304, which may store past test results 108 per user, including aliments and/or other physiological stimuli involved in tests, biomarker levels recorded, or the like. One or more tables in user database 120 may include, without limitation, a proscription table 308, which may be used to store user-specific proscriptions of one or more users as described above. Persons skilled in the art, upon reviewing the entirety of this disclosure, will be aware of various alternative or additional data which may be stored in user database 120, including without limitation any data concerning any user activity, demographics, profile information, viewing and/or media consumption history, or the like.

Referring again to FIG. 1, computing device 104 may be configured to select second training set 124 by receiving at least an element of user data describing the user, identifying a plurality of human subjects matching the at least an element of user data, and selecting the second training set 124 from data representing biomarker impacts on the plurality of human subjects; data sets may be anonymized to forestall issues of privacy. In an embodiment, computing device 104 may receive an expert input, which may be received in any way described above, identifying one or more categories of data, such as demographic data, medical history data, physiological data such as biological extraction data, or the like, with regard to which users having matching or similar data may be expected to have similar immune responses and/or immune effects as a result of consuming food elements and/or other aliments and/or as a result of receipt of one or more physiological stimuli. Identification of plurality of human subjects may be performed by querying a database such as user database 120 for records regarding persons having matching and/or similar values to those of user for such one or more categories of data.

Alternatively or additionally, and still referring to FIG. 1, user and such human subjects may be matched to one another using a user classifier 128 identifying them as mutually similar with respect to the one or more categories of data. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. User classifier 128 may be configured to output identifiers of a bin and/or set of users identified as similar using classification algorithm, where a "identifier" is a datum that labels or otherwise identifies a user set; that is, a label identifying a set of users that have sets of user data, such as without limitation biological extractions, that are clustered together, found to be close under a distance metric as described below, or the like. A user set may be a collection of users having closely related user data regarding one or more categories for classification as described above. User classifier 128 may include a classifier configured to input user data and output user set identifiers.

Further referring to FIG. 1, computing device 104 and/or another device may generate user classifier 128 using a classification algorithm, defined as a processes whereby a computing device 104 derives a classifier from user classification training data. User classifier 128 may be trained by computing device 104 and/or one or more other devices in or communicating with system 100 using training data containing a plurality of sets of data pertaining to a plurality of persons. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, plurality of elements of user data may be utilized by classification algorithms as or in training data. Training data, as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

Still referring to FIG. 1, training data used to generate user classifier 128 may include, without limitation, a plurality of data entries, each data entry including one or more elements of user data such as biological extractions, and one or more correlated user set identifiers, where user set identifiers and associated user data profiles may be identified using feature learning algorithms as described below. Index training data and/or elements thereof may be added to, as a non-limiting example, by classification of multiple users' data to user set identifiers using one or more classification algorithms.

Still referring to FIG. 1, computing device 104 may be configured to generate user classifier 128 using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(AB)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate user classifier 128 using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using Pythagorean norm $$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting example, K-nearest neighbors algorithm may be configured to classify an input vector including a plurality of user data to vectors representing similar users' data.

In an embodiment, and still referring to FIG. 1, computing device 104 may be configured to receive a test result 108 detecting an effect of at least an aliment and/or other at least a physiological stimulus on a rapidly changing biomarker, defined as a biomarker having a value that can change in a measurable and reliable way during a test such as a differential test as described above, and predicting an effect on a chronic biomarker, defined as a biomarker that does not change quickly enough and/or in response to testing as described above, to measure directly in a test, as a function of the effect on the rapidly changing biomarker. In an embodiment, a value, such as a blood value, that responds quickly to consumption of a food or other aliment, and/or receipt of other physiological stimulus, may have resting and/or constant levels correlated with a longer-term blood value/biomarker having an impact on immune system, such that frequent consumption of an aliment, and/or receipt of a physiological stimulus, that increases or decreases the more rapidly changing value may cause and/or be associated with an increase and/or decrease in the more slowly changing chronic biomarker; in an embodiment, computing device 104 may predict that the aliment and/or physiological stimulus has a likely future effect on the slower-changing value. For instance, and without limitation, blood glucose fluctuates depending on food consumption, physical activity, endocrinal factors, and other variables; changes in blood glucose in response to consumption of sugar are readily measurable using a differential test or other test as described above. Continuing the example, HbA1c may fluctuate more slowly, and may correlate to average glucose levels over a period of some weeks or months. In an embodiment, computing device 104 may determine that a given HbA1c may be associated with a more effective immune system and/or immune response as described in further detail below; a test as described above may be used to measure effect of one or more aliments on blood glucose levels, from which computing device 104 may predict an effect of regular consumption of the one or more aliments and/or engagement in exercise, consumption of medication, consumption of supplements, and/or receipt of any other physiological stimulus on HbA1c. In general, computing device 104 may predict an effect of at least an aliment and/or other physiological stimulus on chronic biomarker using a measured effect on rapidly changing biomarker using a mathematical relationship between short-term changes in rapidly changing biomarker and long-term changes in chronic biomarker.

Continuing to refer to FIG. 1, a mathematical relationship between a rapidly changing biomarker and chronic biomarker using a machine-learning process. A "machine learning process," as used in this disclosure, is a process that automatedly uses a body of training data, for instance as described above, to generate an algorithm that will be performed by a computing device 104/module to produce outputs given data provided as inputs; this is in contrast to a non-machine learning software program where the commands to be executed are determined in advance by a user and written in a programming language. Machine-learning processes may be performed, without limitation, as described in U.S. Nonprovisional application Ser. No. 16/375,303, filed on Apr. 4, 2019, and entitled "SYSTEMS AND METHODS FOR GENERATING ALIMENTARY INSTRUCTION SETS BASED ON VIBRANT CONSTITUTIONAL GUIDANCE," the entirety of which is incorporated by reference herein. Machine-learning processes, algorithms, and/or models may be trained using training data; that is, computing device 104 and/or other devices incorporated in and/or communicating with system 100 may train machine-learning processes, algorithms, and/or models using training data.

Still referring to FIG. 1, computing device 104 may determine a mathematical relationship between rapidly-changing biomarker and chronic biomarker using one or more supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include rapidly changing biomarker levels as described above as inputs, chronic biological marker levels as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

Still referring to FIG. 1, computing device 104 and/or another device in system 100 may be designed and configured to perform supervised machine-learning and/or create or use a machine-learning model using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 1, supervised machine-learning algorithms may include, without limitation, linear discriminant analysis. Supervised machine-learning algorithm may include quadratic discriminate analysis. Supervised machine-learning algorithms may include kernel ridge regression. Supervised machine-learning algorithms may include support vector machines, including without limitation support vector classification-based regression processes. Supervised machine-learning algorithms may include stochastic gradient descent algorithms, including classification and regression algorithms based on stochastic gradient descent. Supervised machine-learning algorithms may include nearest neighbors algorithms. Supervised machine-learning algorithms may include Gaussian processes such as Gaussian Process Regression. Supervised machine-learning algorithms may include cross-decomposition algorithms, including partial least squares and/or canonical correlation analysis. Supervised machine-learning algorithms may include naïve Bayes methods. Supervised machine-learning algorithms may include algorithms based on decision trees, such as decision tree classification or regression algorithms. Supervised machine-learning algorithms may include ensemble methods such as bagging meta-estimator, forest of randomized tress, AdaBoost, gradient tree boosting, and/or voting classifier methods. Supervised machine-learning algorithms may include neural net algorithms, including convolutional neural net processes.

Still referring to FIG. 1, models and/or outputs may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

With continued reference to FIG. 1, computing device 104 is configured to determine an immune system impact of the at least an aliment as a function of the at least a biomarker. An "immune system impact," as used in this disclosure, is a quantitative datum illustrating a degree of and/or change in immune system efficacy caused by a given level of and/or change in a biomarker. "Immune system efficacy," as used herein, ability of the immune system to perform its function effectively by fighting off infections, correcting mutations, and neutralizing toxins and foreign bodies, while minimizing negative side effects of over-inflammation, harmful immune reactions such as cytokine storms, and/or autoimmune processes. Immune system efficacy, and impact thereon, may be quantified by expert entries, for instance in the form of probabilities of successful immune response to one or more infections or other threats to a body, and/or rating of efficacy on an absolute and/or relative scale such as a ten-point scale; such entries may be provided by experts using a graphical user interface or the like as described above. Computing device 104 determines immune system impact using a machine-learning process, which may include without limitation any machine-learning process as described above. Machine-learning process is trained, by computing device 104 and/or one or more other devices in and/or communicating with system 100, using a first training set 132 relating biomarker levels to immune system function. Training set, which may include any training data as described above. Training set may, for instance, relate biomarker levels and/or changes in biomarker levels, individually or in combinations of levels and/or changes in levels of multiple biomarkers, to measures of impact on immune efficacy and/or measures of immune efficacy. In a non-limiting example, and as described above, first training set 132 may include a plurality of expert entries associating biomarker levels with immune system function, where immune system function is represented by one or more quantifications of immune system efficacy and/or impact on immune system.

Still referring to FIG. 1, computing device 104 is may select first training set 132 by receiving at least an element of user data describing the user and identify a plurality of data entries matching the at least an element of user data. Identification of data sets may be performed as described above, for instance by querying a user database 120 and/or using a user classifier 128 to select a population of users matching user according to one or more factors and/or categories of data, for instance as provided by experts as described above. Computing device 104 may select first training set 132 from plurality of data entries matching at least an element of user data; this may be accomplished, without limitation, as described above for selection of training data corresponding to a user population matching data of user.

With continued reference to FIG. 1, machine-learning process may include any supervised machine-learning process 136 as described above. For instance, a supervised learning process used as machine-learning process may include one or more biomarker levels and/or changes therein as described above as inputs and immune system impact data as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

Still referring to FIG. 1, computing device 104 is configured to generate a physiological stimulus recommendation using the determined immune system impact. A "physiological stimulus recommendation," as used in this disclosure, is a user-readable display listing one or more physiological stimuli that user should, or should not, receive to improve immune function, including recommendation concerning physiological stimuli that are exercise (referred to herein as an "exercise recommendation"), supplements (referred to herein as a "supplement recommendation"), medication (referred to herein as a "medication recommendation"), lifestyle changes (referred to herein as a "lifestyle recommendation"), or the like. Physiological stimulus recommendation may include a nutritional recommendation 140 using the determined immune system impact. A "nutritional recommendation," as used in this disclosure, is a user-readable display listing one or more foods that user should, or should not, eat to improve immune function. Generation of physiological stimulus recommendation and/or nutritional recommendation 140 may include identification of one or more aliments that user should consume based upon processes described above; selected one or more aliments may be listed on a report and/or instruction set provided to user. Instruction set may convert lists of one or more aliments to narrative language, images, and/or videos as described in further detail below. Nutritional recommendation 140 and/or physiological stimulus recommendation may alternatively or additionally include recipes, meals, meal plans, and/or lists of ingredients made up of recommended aliments, exercise programs, supplement and/or medication consumption, meditation sessions, therapy sessions, and/or other sets and/or schedules for receipt of physiological stimuli, selected for improvement of immune function as described above.

Further referring to FIG. 1, generating nutritional recommendation 140 and/or physiological stimulus recommendation may include identifying an aliment and/or physiological stimulus, of the at least an aliment and/or physiological stimulus, that has a positive immune effect, retrieving a list of related aliments and/or physiological stimuli, and generating a nutritional recommendation 140 and/or physiological stimulus recommendation listing the list of related aliments and/or physiological stimuli. Related aliments may be identified using a cluster of related aliments and/or physiological stimuli as identified using clustering algorithm 116 as described above; in other words, computing device 104 may identify a plurality of related aliments and/or physiological stimuli using the clustering algorithm 116, and generate a nutritional recommendation 140 and/or physiological stimulus recommendation listing the list of related aliments and/or physiological stimuli. Computing device 104 may filter aliments included in nutritional recommendation 140, and/or physiological stimuli included in physiological stimulus recommendation listing using one or more elements of user data, including without limitation user proscriptions, user preferences received from user, or the like. A user may provide user preferences and/or other user data using a user device, for instance by way of a graphical user interface. Computing device 104 may, for instance, maintain a database of meals with food lists, exercise programs, supplement and/or medication consumption, meditation sessions, therapy sessions, and/or other sets and/or schedules for receipt of physiological stimuli, permitting a user and/or computing device 104 to match cluster elements to meals in the database, exercise programs, supplement and/or medication consumption, meditation sessions, therapy sessions, and/or other sets and/or schedules for receipt of physiological stimuli, to generate recommendations. Generation of nutritional recommendations 140 and/or physiological stimulus recommendations, receipt of user preferences, proscriptions, and the like, and provision of nutritional recommendations 140 and/or physiological stimulus recommendation to user, for instance in an alimentary instruction set and/or ameliorative instruction set, may be performed without limitation as described in U.S. Nonprovisional application Ser. No. 16/375,303.

Still referring to FIG. 1, computing device 104 is configured to provide the nutritional recommendation 140 and/or physiological stimulus recommendation to the user, for instance by transmission to and/or display on a user client device; this may be performed without limitation as described in U.S. Nonprovisional application Ser. No. 16/375,303.

Figure 4:
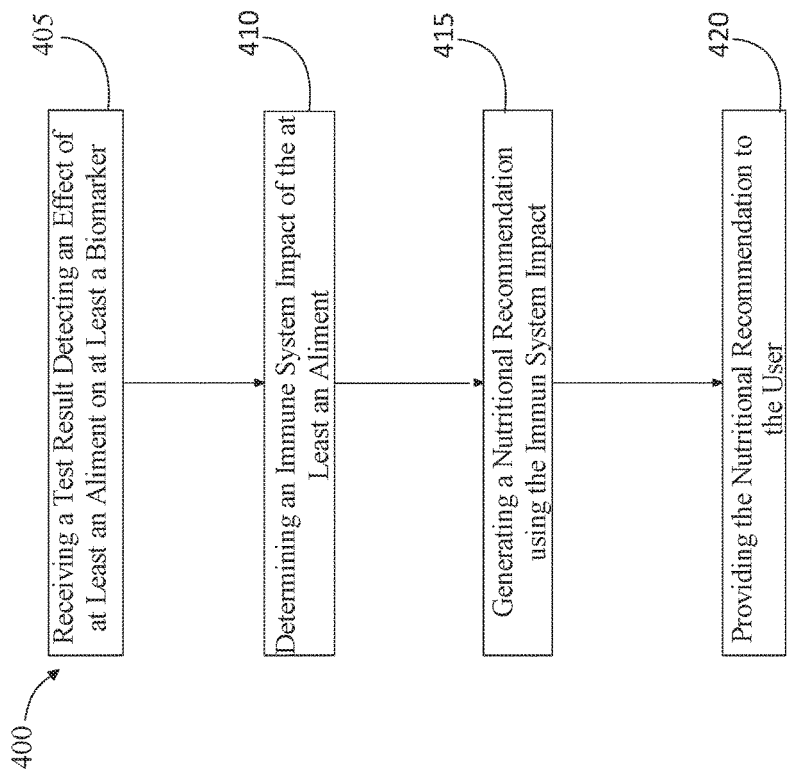
FIG. 4 is a flow diagram of an exemplary embodiment of a method of nutritional recommendation using artificial intelligence analysis of immune impacts.

Referring now to FIG. 4, an exemplary embodiment of a method 400 of nutritional recommendation 140 using artificial intelligence analysis of immune impacts is illustrated. At step 405 a computing device 104 receives a test result 108 detecting an effect of at least an aliment on at least a biomarker; this may be implemented, without limitation, as described above in reference to FIGS. 1-3. Computing device 104 may receive test result 108 by receiving a result of a differential test. Computing device 104 may receive test result 108 by identifying at least cluster of foods having similar biomarker effects to at least an aliment using a clustering algorithm 116 and a second training set 124 representing biomarker impacts on a population of human subjects and selecting as the at least an aliment at least a cluster representative. Selecting at least an aliment may include selecting a first candidate cluster representative, determining a user-specific proscription of the first candidate cluster representative and selecting a substitute item as the cluster representative. Computing device 104 is may select the second training set 124 by receiving at least an element of user data describing the user, identifying a plurality of human subjects matching the at least an element of user data, and selecting the second training set 124 from data representing biomarker impacts on the plurality of human subjects. Computing device 104 may select a cluster representative from each of a plurality of clusters. Receiving the test result 108 may include receiving a test result 108 detecting an effect of at least an aliment on a rapidly changing biomarker and predicting an effect on a chronic biomarker of the effect on the rapidly changing biomarker.

At step 410, and still referring to FIG. 4, computing device 104 determines an immune system impact of the at least an aliment as a function of the at least a biomarker using a machine-learning process, the machine-learning process trained using a first training set 132 relating biomarker levels to immune system function; this may be implemented, without limitation, as described above in reference to FIGS. 1-3. First training set 132 may include a plurality of expert entries associating biomarker levels with immune system function. Computing device 104 may select first training set 132 by receiving at least an element of user data describing user, identifying a plurality of data entries matching the at least an element of user data, selecting the first training set 132 from the plurality of data entries matching the at least an element of user data.

At step 410, and continuing to refer to FIG. 4, computing device 104 generates a nutritional recommendation 140 using the determined immune system impact; this may be implemented, without limitation, as described above in reference to FIGS. 1-3. Generating the nutritional recommendation 140 may include identifying an aliment, of the at least an aliment, that has a positive immune effect; retrieving a list of related aliments and generating a nutritional recommendation 140 listing the list of related aliments.

At step 415, computing device 104 provides nutritional recommendation 140 to user; this may be implemented, without limitation, as described above in reference to FIGS. 1-3.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
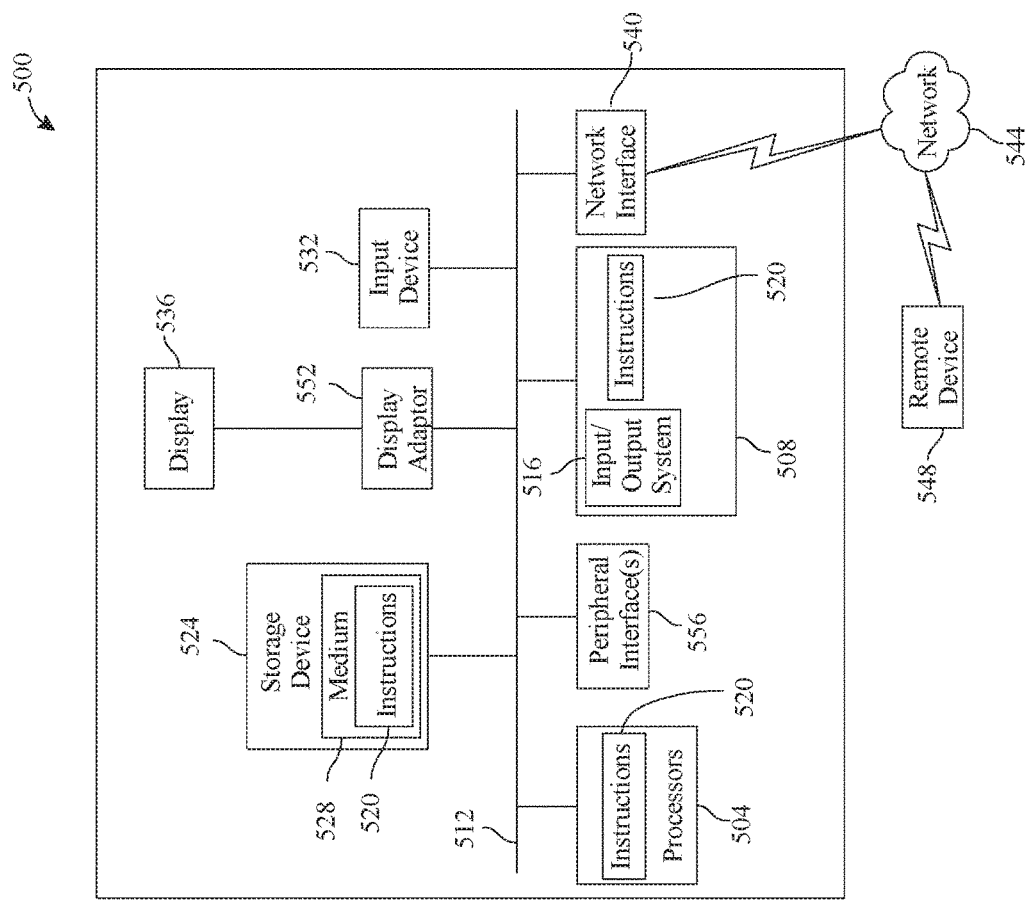
FIG. 5 is a block diagram of a computing system that can be used to implement any one or more of the methodologies disclosed herein and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Processor 504 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 504 may be organized according to Von Neumann and/or Harvard architecture as a non-limiting example. Processor 504 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 508 may include various components (e.g., machine-readable media) including, but not limited to, a random-access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for nutritional recommendation using artificial intelligence analysis of immune impacts, the system comprising a computing device designed and configured to:
   receive a test result detecting an effect of at least an aliment on at least a biomarker;
   generate a supervised machine-learning model, wherein generating the machine-learning model further comprises:
      receiving a first training set, wherein the first training set correlates biomarker levels to immune system function; and
      training, iteratively, a supervised machine-learning process as a function of the first training set to generate the trained machine-learning model;
   generate an immune system impact of the at least an aliment as a function of the supervised machine-learning model, wherein the supervised machine-learning model inputs the effect on the at least a biomarker from the test result and outputs the immune system impact of the at least an aliment;
   generate a clustering model, wherein generating the clustering model further comprises:
      receiving a second training set, wherein the second training set correlates physiological stimuli and biomarker impacts; and
      training, iteratively, a clustering algorithm as a function of the second training set to generate the trained clustering model;
   generate a cluster of physiological stimuli as a function of the clustering model and the effect on the at least a biomarker from the test result;
   generate the at least an aliment as a function of the clustering model, wherein the clustering model inputs the cluster of physiological stimuli and outputs the at least an aliment which is a cluster representative;
   generate a nutritional recommendation as a function of the at least an aliment and the immune system impact of the at least an aliment; and
   provide the nutritional recommendation to a user, wherein generating the clustering model further comprises selecting the second training set, and wherein the second training set is selected by:
      receiving at least an element of user data describing the user;
      identifying a plurality of human subjects matching the at least an element of user data;
      selecting the second training set from data representing biomarker impacts on the plurality of human subjects; and
   determine, successively, the nutritional recommendation to a user; and
   update, successively, the training data with the input to the supervised machine-learning model and the output of the supervised machine-learning model associated with each successive determination of the nutritional recommendation;
   retrain, successively, the supervised machine-learning model with the successively updated training data.

2. The system of claim 1, wherein the computing device is further configured to receive the test result by receiving a result of a differential test.

3. The system of claim 1, wherein generating the clustering model further comprises:
   outputting a first candidate cluster representative;
   determining a user-specific proscription of the first candidate cluster representative; and
   outputting a substitute item, wherein the substitute item is the at least a cluster representative.

4. The system of claim 1, wherein the computing device is further configured to select the cluster representative from each of a plurality of clusters.

5. The system of claim 1, wherein receiving the test result further comprises receiving a test result detecting an effect of at least an aliment on a rapidly changing biomarker and predicting an effect on a chronic biomarker of the effect on the rapidly changing biomarker.

6. The system of claim 1, wherein the first training set further comprises a plurality of expert entries associating biomarker levels with immune system function.

7. The system of claim 1, wherein the computing device is further configured to select the first training set by:
   receiving at least an element of user data describing the user;
   identifying a plurality of data entries matching the at least an element of user data; and
   selecting the first training set from the plurality of data entries matching the at least an element of user data.

8. The system of claim 1, wherein generating the nutritional recommendation further comprises:
   identifying an aliment, of the at least an aliment, that has a positive immune effect;
   retrieving a list of related aliments using a second clustering algorithm; and
   generating a nutritional recommendation listing the list of related aliments.

9. A method of nutritional recommendation using artificial intelligence analysis of immune impacts, the method comprising:
   receiving, by a computing device, a test result detecting an effect of at least an aliment on at least a biomarker;
   generating, by the computing device, a supervised machine-learning model, wherein generating the supervised machine-learning model further comprises:
      receiving a first training set, wherein the first training set correlates biomarker levels to immune system function; and
      training, iteratively, a machine-learning process as a function of the first training set to generate the trained supervised machine-learning model;
   generating, by the computing device, an immune system impact of the at least an aliment as a function of the supervised machine-learning model, wherein the supervised machine-learning model inputs the effect on the at least a biomarker from the test result and outputs the immune system impact of the at least an aliment;

generating, by the computing device, a clustering model, wherein generating the clustering model further comprises:
  receiving a second training set, wherein the second training set correlates physiological stimuli and biomarker impacts; and
  training, iteratively, a clustering algorithm as a function of the second training set to generate the trained clustering model;
generating, by the computing device, a cluster of physiological stimuli as a function of the clustering model and the effect on the at least a biomarker from the test result;
generating, by the computing device, the at least an aliment as a function of the clustering model, wherein the clustering model inputs the cluster of physiological stimuli and outputs the at least an aliment which is a cluster representative;
generating, by the computing device, a nutritional recommendation as a function of the at least an aliment and the immune system impact of the at least an aliment; and
providing, by the computing device, the nutritional recommendation to a user, wherein generating the clustering model further comprises selecting the second training set, and wherein the second training set is selected by:
  receiving at least an element of user data describing the user;
  identifying a plurality of human subjects matching the at least an element of user data;
  selecting the second training set from data representing biomarker impacts on the plurality of human subjects and
  determine, successively, the nutritional recommendation to a user; and
  update, successively, the training data with the input to the supervised machine-learning model and the output of the supervised machine-learning model associated with each successive determination of the nutritional recommendation;
  retrain, successively, the supervised machine-learning model with the successively updated training data.

10. The method of claim 9, wherein receiving the test result further comprises receiving a result of a differential test.

11. The method of claim 9, wherein generating the clustering model further comprises:
  outputting a first candidate cluster representative;
  determining a user-specific proscription of the first candidate cluster representative; and
  outputting a substitute item, wherein the substitute item is the at least a cluster representative.

12. The method of claim 9, further comprising selecting the cluster representative from each of a plurality of clusters.

13. The method of claim 9, wherein receiving the test result further comprises receiving a test result detecting an effect of at least an aliment on a rapidly changing biomarker and predicting an effect on a chronic biomarker of the effect on the rapidly changing biomarker.

14. The method of claim 9, wherein the first training set further comprises a plurality of expert entries associating biomarker levels with immune system function.

15. The method of claim 9, wherein further comprising selecting the first training set by:
  receiving at least an element of user data describing the user;
  identifying a plurality of data entries matching the at least an element of user data; and
  selecting the first training set from the plurality of data entries matching the at least an element of user data.

16. The method of claim 9, wherein generating the nutritional recommendation further comprises:
  identifying an aliment, of the at least an aliment, that has a positive immune effect;
  retrieving a list of related aliments using a second clustering algorithm; and
  generating a nutritional recommendation listing the list of related aliments.

\* \* \* \* \*